United States Patent [19]

Fici

[11] 4,361,570

[45] Nov. 30, 1982

[54] USE OF PYRIDOXINE α-KETOGLUTARATE IN THE PROPHYLAXIS OF HYPERLACTICACIDAEMIA

[75] Inventor: Francesco Fici, Milan, Italy

[73] Assignee: Istituto Luso Farmaco D'Italia S.p.A., Italy

[21] Appl. No.: 300,202

[22] Filed: Sep. 8, 1981

[30] Foreign Application Priority Data

Sep. 22, 1980 [IT] Italy .............................. 24827 A/80

[51] Int. Cl.³ ............................................ A61Y 31/44
[52] U.S. Cl. .................................................... 424/263
[58] Field of Search ........................................ 424/263

[56] References Cited

U.S. PATENT DOCUMENTS 3,784,553  1/1974  Roldan et al. ...................... 424/263

*Primary Examiner*—Stanley J. Friedman
*Attorney, Agent, or Firm*—Ostrolenk, Faber, Gerb & Soffen

[57] ABSTRACT

This invention relates to the use of pyridoxine α-ketoglutarate in the prophylaxis of all those physiological conditions for which is known the possibility of a hyperlacticacidaemic state arising or which are sustained by such state as well as in all those pathological cases for the therapy of which drugs are administered which cause an increase of blood lactic acid, both in human and veterinary medicine. The invention also concerns pharmaceutical compositions characterized in that they contain a pharmacologically effective amount of pyridoxine α-ketoglutarate together with the usual inert non-toxic vehicles.

9 Claims, No Drawings

USE OF PYRIDOXINE α-KETOGLUTARATE IN THE PROPHYLAXIS OF HYPERLACTICACIDAEMIA

DESCRIPTION

This invention relates to the use of pyridoxine α-ketoglutarate in the prophylaxis of hyperlacticacidaemia.

Pyridoxine α-ketoglutarate (hereinafter also referred to as PAK) and its use as a detoxicating agent against isoniazid in the treatment of ammonium chloride induced hyperammoniaemia, as a hepatoprotective substance against carbon tetrachloride, is known from French Pat. No. 6453 M of 1968. Further, said patent also mentions an in vitro metabolic activity, according to which the oxygen consumption, as measured by the Warburg apparatus, for homogenized liver and brain, would be markedly higher than that caused by α-ketoglutaric acid or by pyridoxine alone.

Finally, in said patent a liver restoring activity, as well as an eutrophic acitivy, shown by PAK is also mentioned. According to this French patent, the metabolic properties of PAK display at the liver and brain level.

PAK and its derivatives corresponding to the following formula:

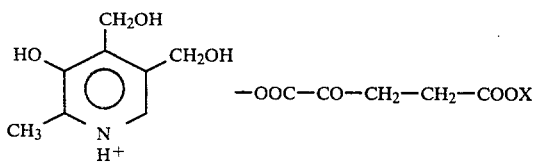

in which X may be a hydrogen atom or an alkali metal or alkaline-earth metal, or an organic base, are the subject of DE-OS No. 1,958,226 of 1969. According to this patent application, PAK and its derivatives corresponding to the above formula are therapeutically useful drugs, since they combine within a single molecule both the pyridoxine and α-ketoglutarate, thus resulting in the increase of the useful activities of these two compounds and in the reduction, in certain cases, of the toxicity thereof.

According to patent application DE-OS No. 1,958,226, PAK and its derivatives show an activity on the nervous system thus finding application in various neurologic states, due to the fact that they intervene in the brain metabolism, as intermediaries, in the following four important roles:

(a) as a substrate in respiration;
(b) as a transamination means for γ-aminobutyric acid (GABA);
(c) as a prosthetic group of a particular decarboxylase which converts glutamic acid to γ-aminobutyric acid;
(d) as a $NH_3$ acceptor in detoxicating processes.

According to the above German patent application, based on these multiform metabolic activities, the pharmacological activity of PAK would be useful in the treatment of the following syndromes:
deficiency symptoms of neurometabolism;
tremor of various origins (senile tremor, idiopathic tremor, Parkinson tremor);
new-born convulsions;
nervous distrubances being treated with isoniazid;
disturbances in neuromuscular processes (in this connection, it is pointed out that "in this field further research is needed");
acute alcoholism.

PAK also shows:
anabolic activity (a remarkable effect on protein synthesis, since it plays an important role in the intermediate aminoacid metabolism; as a consequence of this activity it is suggested that PAK represents an anabolic non-hormonal drug, useful for treating diseases which have a connection with anorexy or possibly weight loss, convalescences, asthenia and the like);
activity on fatty acid metabolism (according to patent application DE-OS No. 1,958,226 a not yet clearly defined relationship occurs between PAK and arteriosclerosis);
activity on haemopoiesis (as a result of its anti-anaemic properties);
activity on coma and precoma, hepatic (due to the possibility for PAK of binding ammonia).

Other indications: according to this DE-OS No. 1,958,226 other indications would exist leading one to assume that PAK may be used also in other cases, such as in gastric hematemesis (particularly in "haematemesis gravidorum"); in the treatment of some skin diseases (eczema, seborhoic dermatitis, "angulus infectiosus"); in the deficiency diseases such as beri-beri and pellagra; in heart diseases which do not respond to the usual therapy.

However, it should be noted that all these suggestions for therapeutical activity are supported by very little or no clinical data, so that the statements relating to said multiform therapeutical activity are, to say the least, to be verified.

It has not been found that administration of PAK is particularly active against arising of hyperlacticacidaemia.

It is well known that hyperlacticacidaemia causes an alteration of the acid-base equilibrium, with consequent more or less severe acidosis which may eventually result in coma.

It is therefore the main object of the present invention to provide the use of PAK in the prophylaxis of hyperlacticacidaemia, in all those physiologic and pathologic situations for which is known the possibility of a hyperlacticacidaemic state arising, or which are sustained by such state, and in all those pathological cases for the therapy of which drugs are administered which cause an increase of blood lactic acid, both in human and veterinary medicine.

A further object of the present invention is that of providing pharmaceutical compositions which, together with suitable non-toxic, pharmaceutically inert vehicles contain PAK as an active agent for the prophylaxis of the above pathological affections. A still further object of the invention is that of providing a process for producing the said pharmaceutical compositions.

A still further object of the present invention is that of providing pharmaceutical compositions in dosage unit form appropriate to the desired mode of administration, e.g. as phials for parenteral use, ampoules for oral use and tablets, the active substance (PAK) content of which corresponding to a fraction or to a multiple of the single dose. The dosage units may, for example, contain 1, 2, 3 or more single doses up to 20, or ½, ⅓ or ¼ of a single dose.

As it appears from the outline above, PAK was known prior to the present invention. However, so far as applicants are aware, PAK was not known to possess the utility in the prophylaxis of all those physiological conditions for which is known the possibility of hyperlacticacidaemic state arising or which are sustained by such state, as well as in all those pathological cases for the therapy of which drugs are administered which cause an increase in blood lactic acid, both in human and veterinary medicine, discovered by applicants.

The term "non-toxic, inert, pharmaceutically suitable vehicles" refers to solid or liquid, diluting or encapsulating filling materials. Some non-limiting examples of such materials are: sugars, such as lactose, glucose and saccharose; starches such as maize and potato starch, cellulose and its derivatives, such as sodium carboxymethylcellulose, ethylcellulose, cellulose acetate; powdered gum tragacanth; malt; gelatine; talc; magnesium stearate; calcium sulfate; polyols such as propylene glycol, glicerine, sorbitol, mannitol and polyethylene glycol; agar-agar; alginic acids; apyrogenic water; isotonic salt solutions and buffer solutions with neutral or weakly acid pH, as well as other non-toxic and compatible materials conventionally used in the pharmaceutical industry for preparing pharmaceutical compositions. Additionally, wetting and lubricating agents such as sodium lauryl sulfate, and dyeing, aromatizing and possibly preserving agents may be present.

In the preparation of the above pharmaceutical compositions, it must always be considered that the pH of the PAK/vehicle(s) mixture must never exceed 7.

The pharmaceutical preparations for the administration of PAK according to this invention are preferably in the form of phials for parenteral use (either i.m. or i.v.), ampoules for oral use, syrups, and tablets.

According to the present invention, the daily dosage for an adult may vary from about 600 mg to about 9200 mg, preferably from 900 to 4600 mg. When PAK is administered in tablet form, it is preferable to administer 1-2 tablets 2-3 times a day; as a syrup, it is preferably to administer a teaspoon of PAK 2-3 times a day; when administration of ampoules for oral use is required, 1-3 small bottles (ampoules) are given each day.

According to the instant invention, for parenteral administration, 1-3 phials a day are preferable. Finally, in the case of venous infusion, 5-20 phials daily are administered in 250-500 ml of either saline or other solutions suitable for this purpose. It must be pointed out that the phials of PAK should never be diluted with solutions of bicarbonate or any other material having a pH value greater than 7.

Acute Toxicity Data

| ($LD_{50}$ - mg/kg) | | |
|---|---|---|
| (a) Rat | | |
| | - os | 4800 |
| | - i.m. | 2329 |
| | - i.p. | 1704 |
| | - i.v. | 588 |
| (b) Mouse | | |
| | - os | 5600 |
| | - i.m. | 2472 |
| | - i.p. | 1590 |
| | - i.v. | 496 |
| (c) Rabbit | | |
| | i.v. | 1050 |

Chronic toxicity data

Administration of 400 mg/kg/os to rats for six months does not cause any collateral nor toxic effect in the various organs.

Systemic tolerability

Administration of 46 mg/kg/i.v. and 460 mg/kg/i.m. to rats and 920 mg/kg/i.m. in the dog, is well tolerated.

Activity on gestation

In pregnant rabbit and rat, oral administration of 1300 mg/kg and of 46 mg/kg/i.m. does not cause any noxious effect in the pregnant female, on the gestation and on the embryo-fetal development.

The preparation of the inventive pharmaceutical compositions will be better clarified by means of some illustrative, but not limiting, examples. These examples represent the process presently preferred by applicant; however, as is well known to anyone skilled in the art, they must not be construed narrowly, since there are many other equally efficient ways for preparing the inventive pharmaceutical compositions of the instant invention.

EXAMPLE 1

Phials for parenteral use

| Composition | |
|---|---|
| pyridoxine α-ketoglutarate | 460 mg |
| water for injectable preparation | q.s. to 5 ml |

Preparation

The operations are carried out in a sterile department. In a stainless steel dissolver provided with a Millipore sterilizing filter, PAK is dissolved in water for injectable preparations. The filtered solution is distributed into phials by using an automatic ampoule filling machine and by dosing 5 ml.

EXAMPLE 2

Ampoules for oral use

| Composition for a 10 ml ampoule | |
|---|---|
| PAK | 0.5 g |
| sorbitol solution | 2.00 g |
| methyl p-hydroxybenzoate | 0.008 g |
| propyl p-hydroxybenzoate | 0.004 g |
| sodium edetate | 0.0025 g |
| sweet orange essence | 0.001 g |
| lemon essence | 0.0001 g |
| saccharose | 4.0 g |
| purified water | q.s. to 10 ml |

Preparation

The purified water and the sorbitol solution are placed in a stainless steel reactor; it is heated to 75° C. and, under stirring, saccharose, methyl p-hydroxybenzoate and propyl p-hydroxybenzoate are added; the mixture is heated to 105° C. and kept at this temperature for 5 minutes. It is cooled to 30° C. and the sodium edete, the pyridoxine α-ketoglutarate, the essence of sweet orange and the essence of lemon are added. The filtered syrup is dosed into small bottles by an automatic machine.

EXAMPLE 3

Syrup

| Composition for 100 ml | |
|---|---|
| PAK | 5 g |
| sorbitol solution | 20.00 g |
| methyl p-hydroxybenzoate | 0.08 g |
| propyl p-hydroxybenzoate | 0.04 g |
| sodium edetate | 0.025 g |
| sweet orange essence | 0.01 g |
| lemon essence | 0.001 g |
| saccharose | 40.00 g |
| purified water | q.s. to 100 ml |

Preparation

The purified water and sorbitol solution are placed in a stainless steel reactor; it is heated to 75° C. and, under stirring, the saccharose, the methyl p-hydroxybenzoate and the propyl p-hydroxybenzoate are added; the mixture is heated to 105° C. and kept at such temperature for 5 minutes. It is cooled to 30° C. and the sodium edetate, the pyridoxine α-ketoglutarate, the sweet orange essence and the lemon essence are added. The filtered syrup is dosed into small bottles by an automatic metering machine.

EXAMPLE 4

Tablets

| Composition for each tablet | |
|---|---|
| PAK | 300 mg |
| polyvinylpyrrolidone | 15 mg |
| stearic acid | 14 mg |
| talc | 25 mg |
| hydroxypropylcellulose | 4 mg |
| titanium dioxide | 2 mg |

Preparation

The PAK is granulated with a water polyvinylpyrrolidone solution. After drying, the granulate, the stearic acid and the talc are added and subjected to mixing. The resulting mixture is compressed in a rotary machine having punches 9 mm in diameter at a weight of 351 mg per tablet.

The tablets are then coated with a film by spraying onto them, in a Glatt WSG 60 Wuster type apparatus, a methylene chloride-ethanol suspension of hydroxypropylcellulose, talc and titanium dioxide.

Prophylactic action of PAK against the arising of hyperlacticacidaemia (A) It is known that administration of metformin causes lacticacidosis in rat. Administration of PAK (25 mg/h by venous infusion) to Wistar male rats weighing 200–220 g, left to fast for 36 hours, causes a notable decrease of lacticacidaemia both when PAK is administered contemporaneously with metformin (300 mg/i.d.) (modality "A") and when it is administered three hours later (modality "B"). The resulting lactate levels are $2.9 \pm 0.8$ mM/l with modality "A" and $1.37 \pm 0.01$ mM/l with modality "B", respectively.

The control animals show a lacticacidaemia level of $5.1 \pm 0.59$ mM/l.

The drug, therefore, prevents hyperlacticacidaemia induced by biguanides.

(B) PAK is administered to 14 insulin dependent patients in order to ascertain whether the drug is able to control the increase in lactic acid in the plasma after muscular stress.

All the patients are being treated with insulin and are in a metabolic compensation.

The trials are performed on double-blind conditions. Each patient is subjected to an isometric stress test at 50% of its maximum ability for one minute. The test is effected after venous infusion, in the same patient, of 250 ml of either physiological solution or of a solution of pyridoxine α-ketoglutarate (2300 mg of active substance in 250 ml of physiological solution).

The samples for measuring the lacticacidaemia are taken from the same arm performing the muscular stress.

Between administrations of the two preparations, physiological solution or PAK solution, a free interval of ½ hour is allowed during which the physiological solution is administered.

The average values for lacticacidaemia are as follows:

| (a) Sequence: physiological solution/PAK | |
|---|---|
| 1. physiological solution | |
| - basal | $0.88 \pm 0.19$ |
| - immediately after stress | $3.12 \pm 0.46$ |
| - after 10 minutes | $1.73 \pm 0.35$ |
| - after 15 minutes | $1.54 \pm 0.30$ |
| 2. PAK | |
| - basal | $0.94 \pm 0.20$ |
| - immediately after stress | $2.62 \pm 0.38$ |
| - after 10 minutes | $1.60 \pm 0.30$ |
| - after 15 minutes | $1.18 \pm 0.30$ |
| (b) Sequence: PAK/physiological solution | |
| 1. PAK | |
| - basal | $0.88 \pm 0.16$ |
| - immediately after stress | $2.03 \pm 0.47$ |
| - after 10 minutes | $1.30 \pm 0.33$ |
| - after 15 minutes | $1.11 \pm 0.29$ |
| 2. physiological solution | |
| - basal | $0.93 \pm 0.19$ |
| - immediately after stress | $2.08 \pm 0.49$ |
| - after 10 minutes | $1.43 \pm 0.44$ |
| - after 15 minutes | $1.25 \pm 0.40$ |

The analysis of the variance shows that:
(a) the stress causes a statistically meaningful increase ($p<0.01$) of lacticacidaemia;
(b) with administration of PAK, the increase ($p<0.01$) is lower with respect to physiological solution;
(c) the reduction of lacticacidaemia is faster with PAK;
(d) the effect of PAK is protracted in time.

Thus, PAK antagonizes the development of a hyperlacticacidaemia due to stress.

(C) Seven diabetic, non-insulin dependent patients are tested for 7 days with sulfanylureas at a therapeutical dosage and for a further 7 days with sulfanylureas combined with PAK, at a dosage of 1.8 g/day/os.

The resultant hematic concentration of lactic acid is markedly lower in 5 of the 7 subjects after administration of the combination.

The average values of lacticacidaemia of these patients, are as follows:
(a) after administration of sulfanylureas: 2.46 mM/l
(b) after administration of sulfanylureas and PAK: 1.16 mM/l The difference is statistically significant ($p < 0.01$) and the lactic acid decrease is of 52.8%.

(D) The administration of 30 mg/kg of body weight of PAK to trained non-athletic individuals increases the maximal aerobic capacity ($V_{O_2}$ max) by 6% ($p < 0.005$). The kinetics of the $V_{O_2}$ on-and-off responses at the onset and offset of a rectangular work load is not affected by the drug. Peak blood lactate concentration [$La_b$] following two supermaximal running work loads lasting 60 seconds and 132±4 seconds, respectively, is significantly ($p < 0.05$ and $p < 0.01$) lower after PAK treatment ($\Delta La_b = -1.1$ and $< 2.7$ mmol·1$^{-1}$, respectively) than that of the control group. The half time (t ½) of La disappearance from blood during recovery is unaffected by PAK (19.7 min vs. 19.5 min). It is concluded that PAK prompts aerobic metabolism probably activating the malateoxaloacetate shuttle and the generation of high energy phosphates at the substrate level.

(E) The venous administration of pyridoxine α-ketoglutarate (2300 mg in 250 ml of physiological solution) to 25 cyrrhotic patients having hyperlacticacidaemia has prevented its further increase and has caused a statistically significant ($p < 0.01$) reduction of such hyperlacticacidaemia with reference to the basal values and with reference to the controls. The lacticacidaemia, in the PAK treated group, has in fact changed from 22.71±1.07 mg% to 15.99±0.73 mg% ($p < 0.01$), whereas in the group treated with the physiological solution it has changed from 21.50±0.85 mg% to 24.72±0.89 mg% ($p < 0.05$). The difference between the active drug and the physiological solution is significant ($p < 0.01$). The tests have been carried out on double blind condition.

(F) For veterinary use, PAK is incorporated into feed or feed premix compositions in effective but non-toxic amounts. Said compositions are then fed to animals, particularly to horses, as disclosed hereinafter.

The feed base most generally used according to the instant invention is bran, oat, forage, roughage feeds such as silage or various commercial grain mixtures commonly used in animals. The quantity of PAK used to supplement such feed base will be a quantity sufficient to antagonize hyperlacticacidaemia due to stress in the animal but not to have a toxic or otherwise noxious effect.

With PAK administration, at a dose of 2 g/100 kg of weight/day for 15 days, to 5 trotters subjected to muscular stress (trot), a significant decrease in the formation of blood lactic acid is obtained.

In fact, the lacticacidaemia before treatment in basal conditions is 6.04 mg/100 ml and immediately after the stress it rises to 29.41 mg/100 ml.

After treatment, the basal lacticacidaemia is 3.30 mg/100 ml and immediately after the stress it is 15.94 mg/100 ml.

I claim:

1. A method for the treatment of hyperlacticacidaemia which comprises administering to an animal or human requiring such treatment an anti-hyperlacticacidaemia effective amount of pyroxidine α-ketoglutarate.

2. The method of claim 1, in which the daily administration is about 600 mg to about 9200 mg.

3. The method of claim 2, in which the daily administration is from 900 to 4600 mg.

4. The method of claim 2, in which the hyperlacticacidaemia is drug induced hyperlacticacidaemia.

5. The method of claim 2, in which the hyperlacticacidaemia is muscular stress induced hyperlacticacidaemia.

6. The method of claim 2, in which said human is an insulin-dependent diabetic.

7. The method of claim 2, in which said human is a diabetic receiving oral hypoglycemic agents.

8. The method of claim 2, wherein said human is a cirrhotic.

9. Process for producing a solid or liquid feed composition for animals characterized in that an effective, but non-toxic anti-hyperlacticucidaemia amount of pyridoxine α-ketoglutarate is mixed with an animal feed.

* * * * *